United States Patent
Afriat et al.

[11] Patent Number: 6,066,326
[45] Date of Patent: May 23, 2000

[54] USE OF A POLYDIMETHYLSILOXANE CONTAINING GLUCOSIDE GROUPS AS A MOISTURIZING AGENT IN A COSMETIC OR DERMATOLOGICAL COMPOSITION

[75] Inventors: Isabelle Afriat, Paris, France; Didier Gagnebien, Westfield, N.J.

[73] Assignee: L'Oreal, Paris, France

[21] Appl. No.: 08/941,650

[22] Filed: Sep. 30, 1997

[30] Foreign Application Priority Data

Sep. 30, 1996 [FR] France ................................. 96-11877

[51] Int. Cl.$^7$ ..................................................... A61K 7/48
[52] U.S. Cl. ...................... 424/401; 424/59; 424/78.02; 514/23; 514/844
[58] Field of Search ...................... 424/401, 59, 78.02; 514/23, 844

[56] References Cited

U.S. PATENT DOCUMENTS

| | | | |
|---|---|---|---|
| 5,428,142 | 6/1995 | O'Lenick, Jr. ............................. | 536/1.1 |
| 5,831,080 | 11/1998 | Sejpka et al. ............................ | 536/124 |

OTHER PUBLICATIONS

Database WPI, Week 9516, Derwent Publications Ltd., London, GB; AN 95–118650, XP002031473, "Reduced oiliness external agent for skin and hair care—contg. organo–polysiloxane seriv. having sugar residue and polyhydric alcoho(s)".

Database WPI, Week 9516, Derwent Publications Ltd., London, GB; NA 95–118954, XP002031474, "Cleaning agent for external application agent for skin, e.g. shampoos—is formed by blending organopolysiloxane deriv(s) having a sugar residue with anionic, ampholytic and/or nonionic surfactant".

Database WPI, Week 9516, Derwent Publications Ltd., London, GB; AN 95–118651, XP002031475, "Emulsification compsn. for external application for anti–sun–tan contg. organopolysiloxane deriv. with sugar residue, polyoxyalkylene modified organopolysiloxane and oil component for skin and hair care".

Primary Examiner—Jyothsna Venkat
Attorney, Agent, or Firm—Oblon, Spivak, McClelland, Maier & Neustadt, P.C.

[57] ABSTRACT

A cosmetic or dermatological composition is described that includes, as moisturizing agent, a polydimethylsiloxane containing glucoside groups of formula (I):

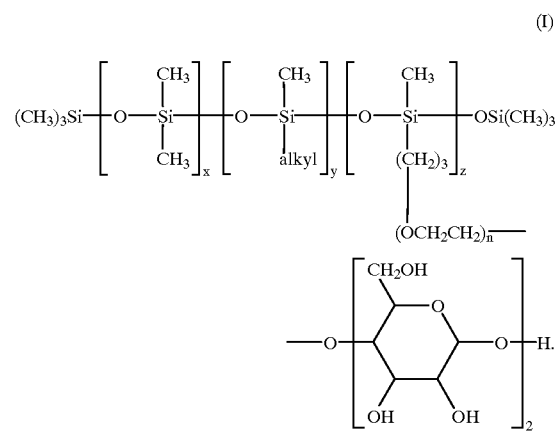

The composition has long-lasting skin moisturization properties. A method is also described for moisturizing the skin and for treating dry skin.

17 Claims, No Drawings

USE OF A POLYDIMETHYLSILOXANE CONTAINING GLUCOSIDE GROUPS AS A MOISTURIZING AGENT IN A COSMETIC OR DERMATOLOGICAL COMPOSITION

BACKGROUND OF THE INVENTION

1. Field of the Invention

The invention relates to the use of a polydimethylsiloxane containing glucoside groups as a moisturizing agent in a cosmetic or dermatological composition. The polydimethylsiloxane compound that contains glucoside groups is especially effective for treating human skin and the scalp, and is particularly effective for moisturizing the skin and treating dry skin.

2. Discussion of the Background

To avoid the ageing of skin, and in order to compensate for the dehydration of exposed skin, it is important to keep the skin well moisturized. Cosmetic and/or dermatological compositions contain suitable active agents that compensate for the dehydration by increasing the amount of water present in the upper layers of the epidermis.

Skin moisturization may be improved by using active agents that supply water to the skin, such as polyols and, in particular, glycerol, glycols and sugars, or alternatively by using active agents that protect the hydrolipid film of the skin by preventing the evaporation of water through a barrier effect.

Large amounts of polyols cannot be added to a cosmetic or dermatological composition without running the risk of obtaining a sticky composition, which discourages users from using the composition. In addition, the duration of the moisturization provided by the polyols is limited in time. Moisturization that lasts for at least one day is sought when a cosmetic product is applied.

The active agents which reinforce the barrier effect are, in particular, hydrocarbon substances such as liquid petroleum jelly. It is generally observed that the desired effect is not obtained immediately after application of the composition, but rather gradually and often only after a few hours.

There is thus a need for active agents having good moisturizing properties, which have long-lasting moisturization properties, and which do not make the composition sticky.

SUMMARY OF THE INVENTION

One object of the present invention is to provide cosmetic or dermatological compositions which have fast-acting moisturizing properties.

Another object of the present invention is to provide a cosmetic or dermatological composition in which a polyol may be introduced in a lower amount and thus obtain a product which is less sticky than those of the prior art.

Another object of the present invention is to provide a dermatological composition for treating the skin.

Another object of the present invention is to provide a cosmetic composition for providing long-lasting moisturization of dry skin.

Another object of the present invention is to provide a dermatological salve or ointment for the therapeutic treatment of dry skin.

These and other objects of the present invention have been achieved with a dermatological or cosmetic composition that includes as an active ingredient at lest one polydimethylsiloxane that contains glucoside groups.

The first embodiment of the present invention is, therefore, a cosmetic or dermatological composition, that includes:

as a skin-moisturizing active ingredient in a cosmetically or dermatologically acceptable medium, at least one polydimethylsiloxane containing glucoside groups, of formula (I):

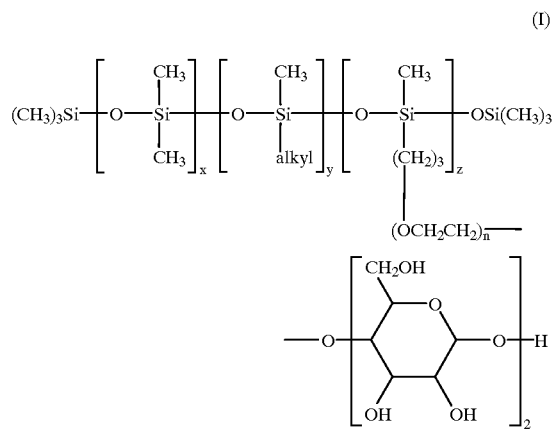

wherein:
x, y and z each represent a positive integer ranging from 1 to 10,000,
n represents a positive integer ranging from 1 to 20,
the alkyl radical represents a linear or branched saturated hydrocarbon radical containing from 2 to 20 carbon atoms.

The second embodiment of the present invention is a method for moisturizing the skin, that includes:

applying to the skin a cosmetic or dermatological composition including, as a skin-moisturizing active ingredient, at least one polydimethylsiloxane containing glucoside groups, of formula (I):

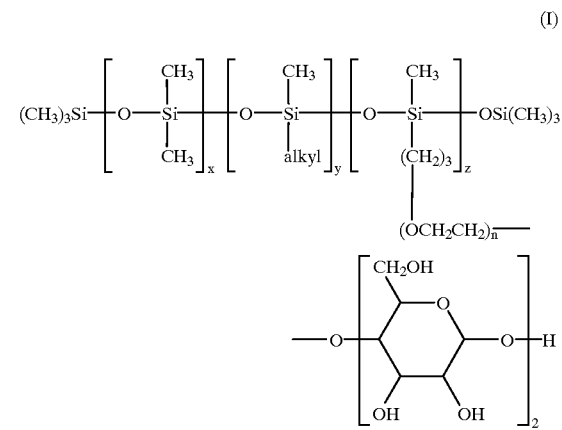

wherein:
x, y and z each represent a positive integer ranging from 1 to 10,000,
n represents a positive integer ranging from 1 to 20,
the alkyl radical represents a linear or branched saturated hydrocarbon radical containing from 2 to 20 carbon atoms.

The third embodiment of the present invention is a method for treating dry skin, that includes:

applying to the skin a cosmetic or dermatological composition including, as a skin-moisturizing active ingredient, at least one polydimethylsiloxane containing glucoside groups, of formula (I):

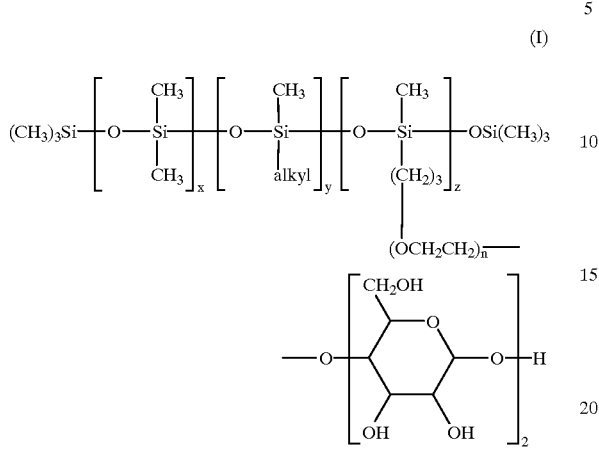

(I)

wherein:

x, y and z each represent a positive integer ranging from 1 to 10,000, n represents a positive integer ranging from 1 to 20, the alkyl radical represents a linear or branched saturated hydrocarbon radical containing from 2 to 20 carbon atoms.

The inventors have surprisingly found that the above-identified compound has unexpected and excellent moisturizing properties and may be used as the active ingredient in a cosmetic or dermatological composition, or in a process for moisturizing the skin.

BRIEF DESCRIPTION OF THE PREFERRED EMBODIMENTS

Various other objects, features and attendant advantages of the present invention will be more fully appreciated as the same becomes better understood from the following detailed description of the preferred embodiments, which have not intended to be limiting thereof.

Polysiloxanes that contain glucoside groups have been described in cosmetic compositions. JP-A-7-41414 describes the use of polysiloxanes bearing glucide residues in a topical moisturizing composition containing polyols; polysiloxanes making it possible to inhibit the greasy feel induced by the polyols. U.S. Pat. No. 5,428,142 describes glucoside silicones having emollient properties, which can be used as very mild surfactants.

However, the above-described references do not describe or suggest that the polydimethylsiloxanes containing glucoside groups of formula (I) can in themselves have moisturizing properties.

Polydimethylsiloxanes are known to be both hydrophobic and permeable to water vapor, which means that they can neither supply water to the skin nor produce a barrier effect on the skin and are therefore, in principle, not suitable for improving the moisturization of the skin. Consequently, it is entirely unexpected that polydimethylsiloxanes can have moisturizing properties.

Thus, the subject of the present invention is the use, as moisturizing active agent in a cosmetic composition for treating the skin, of at least one polydimethylsiloxane containing glucoside groups, of formula (I):

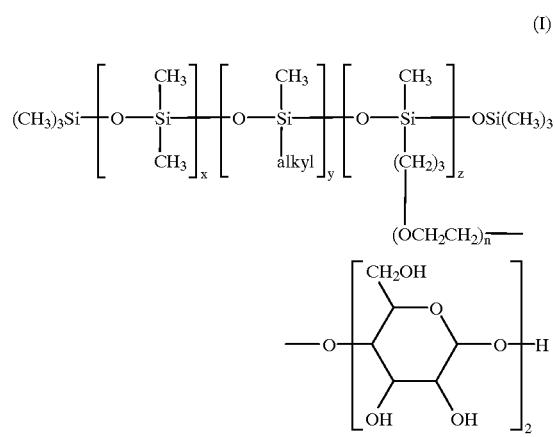

(I)

in which:

x, y and z each represent a positive integer ranging from 1 to 10,000, preferably from 1 to 5000 and, more preferably, from 1 to 2000, n represents a positive integer ranging from 1 to 20, preferably from 1 to 15, the alkyl radical represents a linear or branched saturated hydrocarbon radical containing from 2 to 20 and preferably from 2 to 8 carbon atoms.

In formula (I), the group:

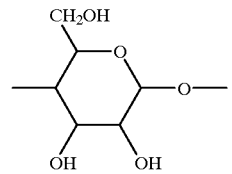

represents the glucoside group.

The subject of the invention is also the use, as moisturizing active agent for the preparation of a dermatological composition intended for treating the skin, of at least one polydimethylsiloxane containing glucoside groups, of formula (I) indicated above.

The subject of the invention is also the use of at least one polydimethylsiloxane containing glucoside groups, of formula (I) indicated above, in a cosmetic composition in order to obtain remanent or long-lasting moisturization of the skin.

The subject of the present invention is also the use of at least one polydimethylsiloxane containing glucoside groups, of formula (I) indicated above, in order to prepare a dermatological ointment or salve intended for the therapeutic treatment of dry skin.

The subject of the invention is also a cosmetic or dermatological process for moisturizing the skin, which consists in applying to the skin a cosmetic composition containing a polydimethylsiloxane containing glucoside groups, of formula (I) indicated above.

The polydimethylsiloxanes containing glucoside groups of formula (I) which may be used according to the invention are, in particular, those mentioned in document EP-A-612,759, in which they are described solely as nonionic emulsifiers which are relatively non-irritating on account of their excellent biodegradability.

In the compounds of formula (I) indicated above, the linear or branched alkyl radical may contain from 2 to 20 and preferably from 2 to 8 carbon atoms. These radicals may be chosen in particular from the methyl, ethyl, n-propyl, isopropyl, n-butyl, isobutyl, tert-butyl, n-pentyl, isopentyl, neopentyl and tert-pentyl radicals, hexyl radicals such as the n-hexyl radical, heptyl radicals such as the n-heptyl radical, and octyl radicals such as the n-octyl and isooctyl radicals.

The polydimethylsiloxane containing glucoside groups of formula (I) according to the invention may, for example, be present in the composition in a concentration ranging from 1.5 to 9% and preferably from 1.8 to 6% of the total weight of the composition. The polydimethylsiloxane containing glucoside groups may be introduced in its existing state into a cosmetically or dermatologically acceptable medium, or alternatively, most usually, it may be introduced into this medium in the form of a solution, in particular in a volatile silicone oil. The amounts indicated above are the amounts of active material (A.M.).

According to a preferred embodiment of the invention, a compound of formula (I) in which the alkyl radical is an n-octyl radical is used as polydimethylsiloxane containing glucoside groups. This compound is sold under the name "SPG 128 VP" by the Wacker Company; it is in the form of a liquid solution containing 15% active material in a cyclomethicone. This solution may be used in a concentration ranging from 10 to 60% and preferably from 12 to 40% of the total weight of the composition.

The composition containing the compound of formula (I) according to the invention is preferably in the form of a water-in-oil emulsion having the appearance of a cream or a milk, which is optionally capable of forming a foam when it is placed under pressure (aerosol), or alternatively in the form of vesicle dispersions containing ionic and/or nonionic lipids. These pharmaceutical forms are prepared according to the usual methods. According to a preferred embodiment, the composition is a fluid emulsion having a viscosity ranging from 3 to 10 poises. However, other pharmaceutical forms such as gels may be envisaged.

The amounts of these various constituents of the composition are those conventionally used in the cosmetic and dermatological fields.

In the composition, the total amount of fatty substance may range from 0.1 to 50% and preferably from 10 to 20% by weight, based on the total weight of the composition. The fatty substances used in the composition are chosen from those conventionally used in the cosmetic or dermatological field.

Preferably, as fatty substances which may be used in the invention, mention may be made, for example, of oils of mineral origin (liquid petroleum jelly), oils of plant origin (apricot oil) and hydrogenated derivatives thereof, oils of animal origin, synthetic oils (hydrogenated polyisobutene), silicone oils (cyclomethicone) and fluoro oils. As other fatty substances, mention may also be made of fatty alcohols, fatty acids and waxes.

The composition may also contain one or more co-emulsifiers, and in particular a polyglycerolated co-emulsifier having an HLB (hydrophilic lipophilic balance) ranging from 4 to 7. Preferably, as polyglycerolated co-emulsifier, mention may be made, for example, of polyglyceryl isostearates and more particularly polyglyceryl-4 isostearate, sold under the name "Isolan G134" by the Goldschmidt Company.

The co-emulsifiers may be present in the composition in an amount ranging from 0.3 to 3% and preferably from 0.5 to 1.5% by weight, based on the total weight of the emulsion.

The cosmetic or dermatological composition according to the invention may also contain common adjuvants in the cosmetic or dermatological field, such as hydrophilic or lipophilic gelling agents, preserving agents, antioxidants, solvents, fragrances, fillers and dyestuffs. It may also contain hydrophilic or lipophilic active agents and organic or inorganic screening agents such as pigments and, in particular, titanium oxide. The amounts of these various adjuvants and active agents are those conventionally used in the fields considered, and, for example, from 0.01 to 20% of the total weight of the composition. Depending on their nature, these adjuvants and active agents may be introduced into the fatty phase, into the aqueous phase and/or into the lipid vesicles.

The composition according to the invention may in particular constitute a cleansing, protective, treatment or care composition for the face, for the neck, for the hands or for the body (for example day creams, night creams, make-up-removing creams, antisun creams or oils, facial or body oils, cleansing milks, make-up-removing milks and body milks), a make-up composition (for example a foundation), an artificial tanning composition or a bath composition.

EXAMPLES

Having generally described this invention, a further understanding can be obtained by reference to certain specific examples which are provided herein for purposes of illustration only and are not intended to be limiting unless otherwise specified.

In all the examples, the compositions are prepared by pouring the oily phase into the aqueous phase with stirring. The amounts indicated are percentages by weight.

Example 1

Moisturizing Fluid

| Oily phase: | |
|---|---|
| SPG 128 VP (containing 15% A.M.) | 20% |
| hydrogenated polyisobutene | 15% |
| Aqueous phase: | |
| glycerol | |
| magnesium sulphate (stabilizer) | 0.7% |
| water | qs 100% |

A fluid having a viscosity of 3 poises, which is capable of moisturizing the skin, is obtained.

Example 2

Make-up-Removing Emulsion

| Oily phase | |
|---|---|
| SPG 128 VP (containing 15% A.M.) | 15% |
| volatile silicone oil | 9% |
| liquid petroleum jelly | 6% |
| Aqueous phase: | |
| glycerol | 5% |
| magnesium sulphate (stabilizer) | 0.7% |
| water | qs 100% |

A fluid moisturizing emulsion which is capable of removing make-up from the skin while at the same time moisturizing the skin for at least 24 hours is obtained.

Example 3
Moisturizing For Antisun Protection

| Oily phase: | |
| --- | --- |
| SPG 128 VP (containing 15% A.M.) | 20% |
| volatile silicone oil | 5% |
| hydrogenated polyisobutene | 5% |
| titanium oxide | 5% |
| Aqueous phase: | |
| glycerol | 5% |
| magnesium sulphate (stabilizer) | 0.7% |
| water | qs 100% |

A fluid emulsion which is capable of protecting the skin against the effects of the sun while at the same time providing moisturization for over at least 24 hours is obtained.

Example 4
Moisturizing Fluid

| Oily phase: | |
| --- | --- |
| SPG 128 VP (containing 15% A.M.) | 20% |
| hydrogenated polyisobutene | 15% |
| polyglyceryl-4 isostearate | 1% |
| Aqueous phase: | |
| glycerol | 5% |
| magnesium sulphate (stabilizer) | 0.7% |
| water | qs 100% |

A fluid capable of moisturizing the skin for several hours is obtained.

Moisturization Test

A test to measure the in vivo moisturization is performed, using a corneometer, on 16 individuals having dry skin. The corneometer is an instrument commonly used for measuring the hydration of the horny layer of the skin. This instrument includes a condenser whose volume varies as a function of the water content of the horny layer.

In order to carry out the test, 2 mg/cm$^2$ of product were applied to the inner side of the forearm of each individual and the moisturization was measured using a corneometer at 1 hour and 24 hours after the application.

A composition according to the invention containing 3% SPG 128 VP active material and 5% glycerol (composition A) and a composition of the prior art containing 3% sugar ester (mixture of methylglucose dioleate, hydrogenated castor oil and beeswax, sold under the name Grillocose 481 by the Grillo Company) and 5% glycerol (composition B) were tested comparatively.

For the 16 individuals, the difference between the moisturization measured one hour after applying the compositions and the moisturization measured 24 hours after applying them was determined and the average of the results obtained was taken:

for composition A according to the invention, this average is 7.375;

for composition B, the average is 10.9375.

The decrease in the moisturization is thus greater with composition B. A paired t test showed that the result was significant to 0.7%.

Thus, this test shows that the polydimethylsiloxane containing glucoside groups according to the invention moisturizes the skin, and does so for a longer period of time than the sugar ester of the prior art.

This application is based on French Patent Application No. 96-11877, filed Sep. 30, 1996, the entire contents of which are hereby incorporated by reference.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. A cosmetic or dermatological composition, comprising:
   at least one co-emulsifier, and
   as a skin-moisturizing active ingredient in a cosmetically or dermatologically acceptable medium,
   at least one polydimethylsiloxane containing glucoside groups, of formula (I):

$$(CH_3)_3Si-\left[O-\underset{\underset{CH_3}{|}}{\overset{\overset{CH_3}{|}}{Si}}\right]_x \left[O-\underset{\underset{alkyl}{|}}{\overset{\overset{CH_3}{|}}{Si}}\right]_y \left[O-\underset{\underset{(CH_2)_3}{|}}{\overset{\overset{CH_3}{|}}{Si}}\right]_z -OSi(CH_3)_3 \quad (I)$$

$$(OCH_2CH_2)_n-\left[\begin{array}{c}CH_2OH\\ \text{sugar ring} \\ OH\ OH\end{array}\right]_2$$

wherein:
   x, y and z each represent a positive integer ranging from 1 to 10,000,
   n represents a positive integer ranging from 1 to 20,
   the alkyl radical represents a linear or branched saturated $C_2$–$C_{20}$ hydrocarbon radical wherein the polydimethylsiloxane containing glucoside groups of formula (I) is present in the composition in an amount of 1.5 to 9% by weight, based on the total weight of the composition.

2. The composition according to claim 1, wherein x, y and z each represent a positive integer ranging from 1 to 5000.

3. The composition according to claim 1, wherein n represents a positive integer ranging from 1 to 15.

4. The composition according to claim 1, wherein the alkyl radical is a saturated $C_2$–$C_8$ hydrocarbon radical.

5. The composition according to claim 1, wherein the alkyl radical is at least one radical selected from the group consisting of methyl, ethyl, propyl, butyl, pentyl, hexyl, heptyl and octyl radicals.

6. The composition according to claim 1, wherein the composition is in the form of a water-in-oil emulsion.

7. The composition according to claim 6, wherein said emulsion is a fluid.

8. The composition according to claim 1, further comprising at least one polyol.

9. The composition according to claim 8, wherein said polyol is glycerol.

10. The composition according to claim 1, wherein said co-emulsifier is a polyglyceryl isostearate.

11. A method for moisturizing the skin, comprising:
applying to the skin a cosmetic or dermatological composition comprising,
at least one co-emulsifier, and
as a skin-moisturizing active ingredient, at least one polydimethylsiloxane containing glucoside groups, of formula (I):

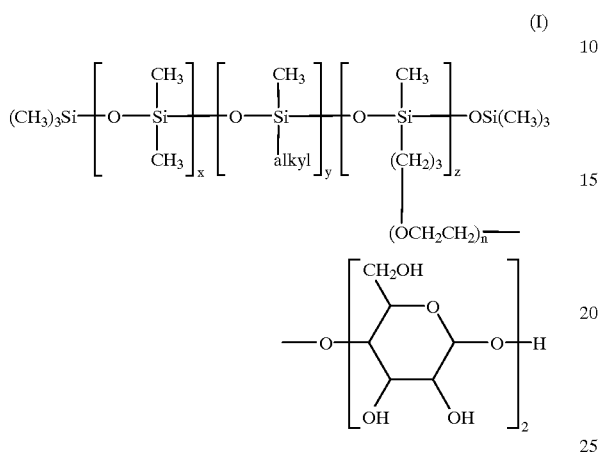

(I)

wherein:
x, y and z each represent a positive integer ranging from 1 to 10,000,
n represents a positive integer ranging from 1 to 20,
the alkyl radical represents a linear or branched saturated $C_2$–$C_{20}$ hydrocarbon radical.

12. The method according to claim 11, wherein x, y and z each represent a positive integer ranging from 1 to 5000.

13. The method according to claim 11, wherein n represents a positive integer ranging from 1 to 15.

14. The method according to claim 11, wherein the alkyl radical is a saturated $C_2$–$C_8$ hydrocarbon radical.

15. The method according to claim 11, wherein the polydimethylsiloxane containing glucoside groups of formula (I) is present in the composition in an amount of 1.5 to 9% by weight, based on the total weight of the composition.

16. The method according to claim 11, further comprising at least one polyol.

17. A method for treating dry skin, comprising:
applying to the skin a cosmetic or dermatological composition comprising,
at least one co-emulsifier, and
as a skin-moisturizing active ingredient, at least one polydimethylsiloxane containing glucoside groups, of formula (I):

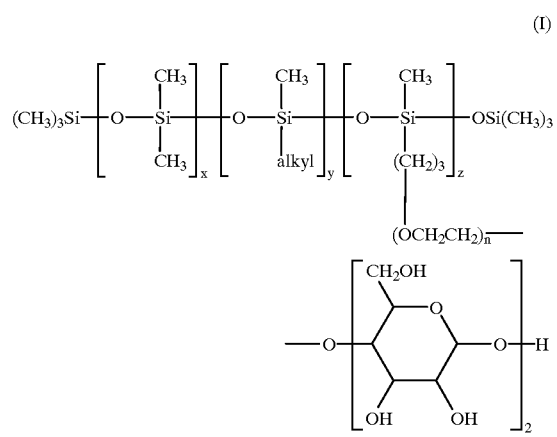

(I)

wherein:

x, y and z each represent a positive integer ranging from 1 to 10,000, n represents a positive integer ranging from 1 to 20, the alkyl radical represents a linear or branched saturated $C_2$–$C_{20}$ hydrocarbon radical.

* * * * *

UNITED STATES PATENT AND TRADEMARK OFFICE
CERTIFICATE OF CORRECTION

PATENT NO.  : 6,066,326
DATED       : May 23, 2000
INVENTOR(S) : Isabelle Afriat et al.

Page 1 of 1

It is certified that error appears in the above-identified patent and that said Letters Patent is hereby corrected as shown below:

Column 6,
Lines 32-49, should read

Signed and Sealed this

Twenty-seventh Day of November, 2001

Attest:

NICHOLAS P. GODICI
Attesting Officer    Acting Director of the United States Patent and Trademark Office

UNITED STATES PATENT AND TRADEMARK OFFICE
CERTIFICATE OF CORRECTION

PATENT NO.    : 6,066,326
DATED         : May 23, 2000
INVENTOR(S)   : Isabelle Afriat et al.

It is certified that error appears in the above-identified patent and that said Letters Patent is hereby corrected as shown below:

Column 6,
Lines 32-49,

" Example 1
Moisturizing Fluid

| Oily phase: | |
|---|---|
| SPG 128 VP (containing 15% A.M.) | 20% |
| hydrogenated polyisobutene | 15% |
| Aqueous phase: | |
| glycerol | |
| magnesium sulphate (stabilizer) | 0.7% |
| water | qs 100% |

A fluid having a viscosity of 3 poises, which is capable of moisturizing the skin, is obtained. "

should read --    Example 1
Moisturizing Fluid

| Oily phase: | |
|---|---|
| SPG 128 VP (containing 15% A.M.) | 20% |
| hydrogenated polyisobutene | 15% |
| Aqueous phase: | |
| glycerol | 5% |
| magnesium sulphate (stabilizer) | 0.7% |
| water | qs 100% |

A fluid having a viscosity of 3 poises, which is capable of moisturizing the skin, is obtained. --

This certificate supersedes Certificate of Correction issued November 27, 2001.

Signed and Sealed this

Twentieth Day of August, 2002

*Attest:*

*Attesting Officer*

JAMES E. ROGAN
*Director of the United States Patent and Trademark Office*